US010524651B2

(12) United States Patent
McGrath et al.

(10) Patent No.: US 10,524,651 B2
(45) Date of Patent: Jan. 7, 2020

(54) INSERTION SECTION FOR LARYNGOSCOPE WITH LATERAL TUBE GUIDE

(71) Applicant: Aircraft Medical Limited, Edinburgh (GB)

(72) Inventors: Matthew John Ross McGrath, Edinburgh (GB); Morgan James Walker, Aarhus (DK)

(73) Assignee: Aircraft Medical Limited, Edinburgh (GB)

( * ) Notice: Subject to any disclaimer, the term of this patent is extended or adjusted under 35 U.S.C. 154(b) by 0 days.

(21) Appl. No.: 15/204,873

(22) Filed: Jul. 7, 2016

(65) Prior Publication Data

US 2016/0317011 A1 Nov. 3, 2016

Related U.S. Application Data

(63) Continuation of application No. 13/254,584, filed as application No. PCT/GB2010/050377 on Mar. 3, 2010, now abandoned.

(30) Foreign Application Priority Data

Mar. 3, 2009 (GB) .................................. 0903610.4

(51) Int. Cl.
*A61B 1/267* (2006.01)
*A61M 16/04* (2006.01)
(Continued)

(52) U.S. Cl.
CPC .......... *A61B 1/267* (2013.01); *A61B 1/00032* (2013.01); *A61B 1/00052* (2013.01);
(Continued)

(58) Field of Classification Search
CPC ....... A61B 1/267; A61B 1/00179; A61B 1/05; A61B 1/06; A61B 1/07; A61M 16/0488
(Continued)

(56) References Cited

U.S. PATENT DOCUMENTS 4,832,020 A * 5/1989 Augustine ......... A61M 16/0488
128/207.14
5,038,766 A 8/1991 Parker
(Continued)

FOREIGN PATENT DOCUMENTS

CN 1051511 A 5/1991
EP 1982640 A 10/2008
(Continued)

OTHER PUBLICATIONS

European Examination Report for European Application No. 10711451.4 dated Jun. 30, 2016; 4 pgs.

*Primary Examiner* — David W Bates
*Assistant Examiner* — Marcela I Shirsat
(74) *Attorney, Agent, or Firm* — Fletcher Yoder P.C.

(57) ABSTRACT

A laryngoscope insertion section for a laryngoscope, which is typically a video laryngoscope, includes a lateral tube guide configured to retain an endotracheal tube in a plane. A viewing port for a camera or other image collector is laterally displaced from the plane of the endotracheal tube. The said plane of the endotracheal tube is aligned substantially in the same plane as a patient's median plane and the tube can be advanced into the larynx using a natural curving motion similar to the motion used to introduce an endotracheal tube using a convention laryngoscope. In a preferred embodiment, the distal tip of the insertion section and a retained endotracheal tube will be located in the patient's median plane during intubation. As the tube guide retains
(Continued)

endotracheal tubes substantially in a plane, lateral curvature is avoided, reducing resistance to advancement of the tube.

12 Claims, 4 Drawing Sheets

(51) Int. Cl.
*A61B 1/00* (2006.01)
*A61B 1/04* (2006.01)
*A61B 1/06* (2006.01)
*A61B 1/07* (2006.01)

(52) U.S. Cl.
CPC ...... *A61B 1/00087* (2013.01); *A61B 1/00105* (2013.01); *A61B 1/04* (2013.01); *A61B 1/06* (2013.01); *A61M 16/0488* (2013.01); *A61B 1/07* (2013.01)

(58) Field of Classification Search
USPC ........ 600/185, 188–189, 196–197, 199, 191, 600/193–194, 237, 120; 128/200.26, 128/207.14
See application file for complete search history.

(56) References Cited

U.S. PATENT DOCUMENTS

| | | | |
|---|---|---|---|
| 5,042,469 A * | 8/1991 | Augustine | A61M 16/0488 128/200.26 |
| 5,203,320 A * | 4/1993 | Augustine | A61M 16/0488 128/200.26 |
| 5,235,970 A * | 8/1993 | Augustine | A61M 16/04 128/200.26 |
| 5,665,052 A | 9/1997 | Bullard | |
| 6,718,970 B2 | 4/2004 | Sniadach | |
| D619,248 S * | 7/2010 | Yokota | D24/137 |
| 7,988,622 B2 | 8/2011 | Gandarias | |
| 8,079,951 B2 | 12/2011 | Yokota et al. | |
| 8,366,612 B2 | 2/2013 | Rosenthal | |
| 9,179,831 B2 * | 11/2015 | McGrail | A61B 1/00016 |
| 9,226,651 B2 * | 1/2016 | McGrath | A61B 1/267 |
| 9,414,743 B2 * | 8/2016 | McGrath | A61M 16/0488 |
| 2002/0117171 A1 * | 8/2002 | Parker | A61M 16/0488 128/200.26 |
| 2004/0019256 A1 | 4/2004 | Cubb et al. | |
| 2006/0276694 A1 * | 12/2006 | Acha Gandarias | A61B 1/015 600/194 |
| 2007/0106117 A1 | 5/2007 | Yokota et al. | |
| 2007/0106121 A1 * | 5/2007 | Yokota | A61B 1/00052 600/188 |
| 2007/0106122 A1 * | 5/2007 | Yokota | A61B 1/00048 600/188 |
| 2009/0032016 A1 * | 2/2009 | Law | A61M 16/0488 128/200.26 |
| 2010/0256451 A1 | 10/2010 | McGrath et al. | |
| 2011/0077466 A1 | 3/2011 | Rosenthal | |

FOREIGN PATENT DOCUMENTS

| | | |
|---|---|---|
| GB | 2431539 A | 4/2007 |
| JP | 2006-087840 A | 4/2006 |
| JP | 2006-326111 A | 12/2006 |
| JP | 2007-117116 A | 5/2007 |
| JP | 2009-523586 A | 6/2009 |
| WO | 2004073510 A1 | 9/2004 |

* cited by examiner

INSERTION SECTION FOR LARYNGOSCOPE WITH LATERAL TUBE GUIDE

CROSS REFERENCE TO RELATED APPLICATIONS

This application is a continuation of U.S. patent application Ser. No. 13/254,584, filed on Nov. 18, 2011 which is the U.S. national phase of International Application No. PCT/GB2010/050377 filed Mar. 3, 2010 which designated the U.S. and claims priority to GB Patent Application No. 0903610.4 filed 3 Mar. 2009, which are incorporated herein by reference in their entirety.

FIELD OF THE INVENTION

The present invention relates to the field of insertion sections for laryngoscopes which include lateral tube guides for detachably retaining and guiding endotracheal tubes during intubation.

BACKGROUND TO THE INVENTION

Laryngoscopes are medical devices which are employed to introduce endotracheal tubes into patient's airways, for example, when a patient is being anaesthetised. Laryngoscopes comprise insertion sections, which are the part of a laryngoscope which extends towards and into a patient's oral cavity during intubation. Insertion sections may be removably attachable to a laryngoscope body, integral parts of laryngoscopes or themselves function as laryngoscopes. As well as an insertion section, laryngoscopes typically comprises a handle which is usually elongate and which may be arranged at an angle to the proximal end of the insertion section or generally parallel to the proximal end of the insertion section, or at any angle therebetween. Laryngoscopes further include a source of light and the invention relates to insertion sections for laryngoscopes which further include an image collector. The image collector might collect video images and may, for example, be a video camera or a fibre-optic bundle for conducting an image to an external video camera, arranged to enable a user to view the distal tip of an endotracheal tube as it is being introduced into a patient's larynx. Laryngoscopes which collect video images are referred to as video laryngoscopes. However, laryngoscopes may also include image collectors which are the distal tip of an imaging arrangement including optical components such as one or more prisms or mirrors, to enable intubation to be viewed by eye, without use of a camera.

Video laryngoscope insertion sections may have integral image collectors, for example, an image collector located on the surface of the insertion section. However, light permeable laryngoscope insertion sections may be demountably attachable to an insertion section retaining member of the laryngoscope and the laryngoscope may comprise an image collector operable to receive images through a light permeable and typically transparent region of a demountable attachable insertion section. Video laryngoscopes may include a display for displaying images collected by the image collector, or an output for communication images to an external display device.

Traditional laryngoscope insertion sections, such as insertion sections known in the art as Miller, Macintosh or Wisconsin blades, function to lift a patient's tissue adjacent the epiglottis to enable a tube to be inserted into a patient's larynx and to enable the patient's larynx to be viewed during intubation. However, they do not guide tubes as such.

It has been proposed to provide laryngoscope insertion sections with tube guides, for example lateral tube guides. By a lateral tube guide we refer to a tube guide which guides an endotracheal tube along a lateral side of the insertion section along at least the majority of the length of the insertion section, to the location from where a retained endotracheal tube extends distally from the tube guide. Lateral tube guides are preferable to tube guides located on the inferior surface (i.e. the surface facing a patient's tongue in use) of an insertion section as they reduce bulk in a plane parallel to a patient's midsagittal plane in use.

A video laryngoscope having an insertion section with a lateral tube guide is disclosed in GB 2 431 539 (Pentax). A laryngoscope having an insertion section with a lateral tube guide is also known from WO 04/073510 (Gandarias), although this publication does not disclose a video laryngoscope. Insertion sections for video laryngoscopes having lateral tube guides are also disclosed in our co-pending international application PCT/GB2008/002900.

A disadvantage of known video laryngoscope insertion sections with lateral tube guides relates to the orientation at which a retained tube extends from the distal end of the insertion section. When adding a lateral tube guide to an insertion section which includes an image collector or through which an image collector gathers images, it is natural to add the tube guide to the side of the image collector. This is particularly true when using an image collector which is integral to an endoscope. Thus, proposed configurations have an optical arrangement as shown in FIGS. 6 and 7, in which the centre of the field of view of the image collector and the line along which the tube guide guides an endotracheal tube from the distal end of the insertion section are each at an angle to the median plane of the insertion section, so as to converge at approximately the location of a patient's larynx in use.

However, there are a number of disadvantages associated with this arrangement. Firstly, users of laryngoscopes have typically been trained using conventional Macintosh laryngoscopes and are used to holding an endotracheal tube (which is typically inherently gently curved) in their free hand and introducing it using a smooth curving motion. Accordingly, the movement which is required to advance the tube along the tube guide is not a natural movement. Secondly, the distal tip of the endotracheal tube appears to move both sideways and upwards simultaneously in the field of view of the image collector. This can make it more difficult for a user to be confident that a retained endotracheal tube is being guided along the correct path to be inserted into the larynx. Thirdly, in some patient's the larynx will be further anterior of the epiglottis than normal. In such patient's a tube guide which advances a tube at an angle to a patient's midline will not advance the tube into the patient's larynx without undesirable manipulation. Furthermore, the endotracheal tube is guided along a path including at least some curvature in a lateral direction. This curvature leads to a resistance to movement of the endotracheal tube in a distal direction. As a result, insertion of the endotracheal tube is made more difficult.

Thus, the invention aims to provide laryngoscopes (typically video laryngoscopes) with tube guides and insertion sections with tube guides for laryngoscopes (typically video laryngoscopes) which overcome some or all of these problems.

SUMMARY OF THE INVENTION

According to a first aspect of the present invention there is provided a laryngoscope insertion section having a proximal end and a distal end for insertion into a patient's oral cavity, the insertion section comprising a viewing port to enable an image collector to collect images of a patient's larynx during intubation, and a tube guide for retaining an endotracheal tube and guiding a retained endotracheal tube towards a patient's larynx, wherein the tube guide is configured to retain an endotracheal tube in a plane, at least in a region including the most distal location where the insertion section contacts a retained endotracheal tube, and the viewing port is laterally offset from the said plane.

As the endotracheal tube is retained in a plane, the endotracheal tube can be advanced in a distal direction, towards a patient's larynx, without lateral curvature, thereby reducing resistance to movement. Furthermore, the said plane of a retained endotracheal tube can readily be aligned with a patient's median plane, so that, once the laryngoscope insertion section has been introduced correctly into a patient's oral cavity and the larynx exposed, further manipulation of the orientation of the insertion section is unlikely to be required. In embodiments where the endotracheal tube is manually advanced, rather than advanced by automatic or semi-automatic means, the hand motion required to advance the endotracheal tube into the larynx is a natural movement, similar to the movement required to introduce an endotracheal tube using traditional laryngoscopes. Preferably, the tube guide is configured so that the retained endotracheal tube continues in said plane distally of the most distal location where a retained endotracheal tube contacts the insertion section.

It may be that the tube guide is configured to retain the endotracheal tube along a region of the insertion section from a location distal of the most proximal location where the insertion section contacts a retained endotracheal tube to the most distal location where the insertion section contacts a retained endotracheal tube. By retaining the endotracheal tube in a plane along a region extending to the most distal location where the insertion section contacts a retained endotracheal tube, the retained endotracheal tube will typically extend distally of the most distal location where the insertion section a retained endotracheal tube within the same plane.

However, it may be that the tube guide is configured to retain the endotracheal tube in the said plane from the most proximal to the most distal location where the insertion section contacts a retained endotracheal tube.

Preferably, the insertion section is configured such that, when the insertion section has been inserted into the oral cavity and located to insert a guided endotracheal tube into a patient's larynx, the said plane is co-planar with the patient's median plane.

In order for the insertion section to be configured in this way, the most distal patient contacting inferior surface of the insertion section (typically the distal tip of the insertion section) is preferably directly inferior or superior of a portion of a retained endotracheal tube. More preferably, the most distal patient contacting inferior surface of the insertion section (typically the distal tip of the insertion section) is in the said plane. Thus, as the most distal patient contacting inferior surface of the insertion section is used to lift the tissue adjacent the epiglottis during intubation, and as a user would typically lift the said tissue in a region centered on the patient's median plane, the most distal patient contacting inferior surface of the insertion section is located in the same plane as the retained endotracheal tube. Thus, a retained endotracheal tube will be located in the patient's median plane while it is advanced in a distal direction into the larynx. The insertion section typically comprises a spatulate member on the inferior surface thereof, wherein the spatulate member typically comprises the said most distal patient contacting inferior surface of the insertion section (and typically also the said distal tip of the insertion section).

Within this specification and the appended claims, the inferior surface is the surface of an insertion section which faces the patient's tongue in use. The opposite surface is referred to as the superior surface. Words such as inferior, inferiorly, superior and superiorly are used in corresponding senses. A superior-inferior axis is a virtual axis extending parallel to the superior and inferior directions. Distal refers to the direction generally away from a user of the insertion section and proximal refers to the direction generally towards a user of the insertion section.

The viewing port is preferably arranged so that an image collector can view insertion of an endotracheal tube into a patient's larynx. Typically, the viewing port has a normal which intersects the said plane distally of the distal tip of the insertion section so as to facilitate viewing of the insertion of a retained endotracheal tube into a patient's larynx.

The laryngoscope is preferably a video laryngoscope. In this case, the image collector may be a video camera, such as a CCD or CMOS video camera. The image collector may be a window or lens terminating an optical conduit, such as one or more optical fibres, for conducting images to a video camera.

The viewing port may be a light transmitting surface of the insertion section, such as a window or a lens of an image collector which is integral to, or detachably removable from, the insertion section. The viewing port could be an external surface of a prism. The viewing port may be part of a continuous light permeable (typically transparent) surface of the insertion section. The viewing port may be a light transmitting surface, such as a window or a lens, through which an image collector can collect images during intubation.

The insertion section may comprise an image collector. In this case, the viewing port may be an image receiving surface of the image collector. The image collector may be demountably attachable to the insertion section. The insertion section may be demountably attachable to an insertion section retaining element of a laryngoscope and may comprise an elongate cavity through which an image collector can be located within the insertion section in use so as to collect images through the viewing port. The insertion section preferably protects (e.g. seals) an image collector within the said elongate cavity from fluids within the oral cavity during intubation. The insertion section may be disposable.

Where the image collector is demountably attachable to the insertion section, for example where the insertion section and image collector are separately mountable to a laryngoscope body, the insertion section preferably comprises a recess to locate the image collector and align the image collector such that it receives images in a field of view including a point in the said plane, distal of the insertion section, where a retained endotracheal tube would enter into a patient's larynx during intubation. Preferably, the distal surface of the viewing port is oriented such that the normal of the distal surface of the viewing port intersects the said plane of a retained endotracheal tube distally of (and typically also superiorly of) the distal tip of the insertion section.

Preferably, the tube guide is adapted to retain an endotracheal tube in the said plane and to allow a retained endotracheal tube to be removed laterally from the tube guide. Thus, the retained endotracheal tube can be disengaged from the tube guide after intubation enabling the insertion section to be moved laterally of the endotracheal tube and removed from the oral cavity.

Preferably, the tube guide is adapted to retain an endotracheal tube such that it is curved, within the said plane, from the most proximal location at which it contacts the insertion section to the most distal location at which it contacts the insertion section. Thus, the endotracheal tube can be advanced by a user with a curved motion of one hand, in a similar fashion to the way in which endotracheal tubes are introduced with traditional laryngoscopes.

The insertion section may comprise an elongate support member and a plurality of tube guiding members extending laterally from the elongate support member to contact the inferior or superior surface of a retained endotracheal tube. The elongate support member may be located in a plane parallel but spaced apart from the said plane. Preferably, the tube guiding members are arrange to leave exposed either the inferior or the superior surface of a retained endotracheal tube at at least one location between the most proximal location where the insertion section contacts a retained endotracheal tube and the most distal location where the insertion section contacts a retained endotracheal tube. Preferably, there is at least one location between the most proximal location where the insertion section contacts a retained endotracheal tube and the most distal location where the insertion section contacts a retained endotracheal tube where both the inferior and superior surfaces of a retained endotracheal tube are left exposed. These arrangements minimise the bulk of the tube guide and thereby reduce the bulk of the insertion section, facilitating safe use of the insertion section in the confined space of a patient's oral cavity.

The tube guide may be arranged to retain an endotracheal tube under flexural tension continuously from the most proximal location where the insertion section contacts a retained endotracheal tube to the most distal location where the insertion section contacts a retained endotracheal tube. This can facilitate retention of the endotracheal tube by tube guiding members extending laterally from an elongate support member, reducing the number and/or bulk of tube guiding members. Preferably, the tube guide is a tube guide for removably retaining an endotracheal tube.

According to a second aspect of the invention there is provided a laryngoscope having an insertion section retaining formation to demountably retain an insertion section according to the first aspect of the invention. The invention also extends to a laryngoscope comprising a handle and an insertion section according to the first aspect of the invention fixedly attached thereto.

The laryngoscope preferably comprises a light source. The elongate cavity may be operable to encompass the light source in use and the insertion section may comprise a translucent or transparent portion to enable light from the light source to be shone on a patient's larynx in use. Thus, the insertion section may function to protect the light source from contact with bodily fluids and/or air during use.

The light source may be a light generating device, for example a light emitting diode or a bulb. The light source may be a light emitting region of a light conduit operably connected to or connectable to a light generating device.

The laryngoscope preferably comprises an image collector. The elongate cavity may be adapted to encompass an image collector in use. The image collector may be a camera. The image collector may comprise a light collecting region of a light conduit and the light conduit may be operable to conduct light to a camera.

The laryngoscope may comprise an elongate image collector support which extends from the body of the laryngoscope and which comprises the image collector. The elongate image collector support may be flexible. The elongate image collector support may be substantially rigid and function as a rigid strengthening element. The The laryngoscope may comprise an elongate image collector support including the image collector and arranged to extend into the elongate cavity in use so as to collect images of a region including a patient's larynx during intubation. The laryngoscope and insertion section may be configured so that the elongate image collector support extends in a plane which is parallel to but spaced apart from the said plane.

The elongate image collector support may comprise a rigid strengthening element. For example, it may comprise an elongate rigid metal housing. The light source may also be mounted in or on the elongate image collector. However, the elongate image collector support may be flexible.

The invention also extends in a third aspect to a kit comprising a laryngoscope according to the second aspect of the invention and an insertion section according to the first aspect of the invention. The insertion sections may be disposable.

In a fourth aspect the invention extends to a method of intubating a patient comprising the steps of using a laryngoscope according to the second or third aspect of the invention, with an endotracheal tube retained in the tube guide, to lift the tissue adjacent a patient's epiglottis and to obtain a view of the patient's larynx, using the image collector, such that the retained endotracheal tube is co-planar with the patient's median plane and advancing the endotracheal tube into the patient's larynx.

Preferably, the method comprises the step of aligning the most distal patient contacting inferior surface of the insertion section with the patient's median plane before the retained endotracheal tube is advanced.

DESCRIPTION OF THE DRAWINGS

An example embodiment of the present invention will now be illustrated with reference to the following Figures in which.

DETAILED DESCRIPTION OF AN EXAMPLE EMBODIMENT

An example embodiment of the invention will now be described with reference to an insertion section having one or more moveable tube guiding members. However, the invention is equally applicable to insertion sections having only fixed tube guiding members.

Figure 1:
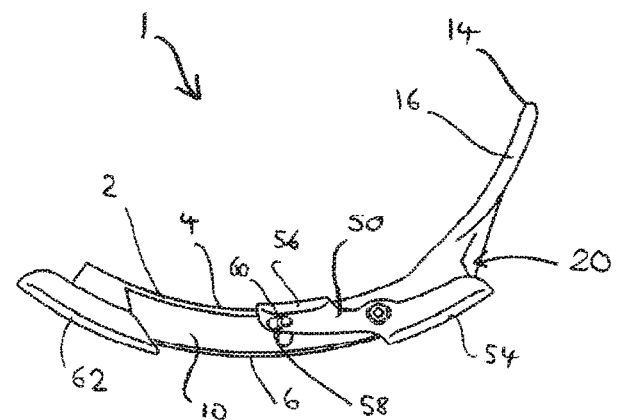
FIG. 1 is a side view of a laryngoscope insertion section having a moveable tube guiding member.
Figure 2:
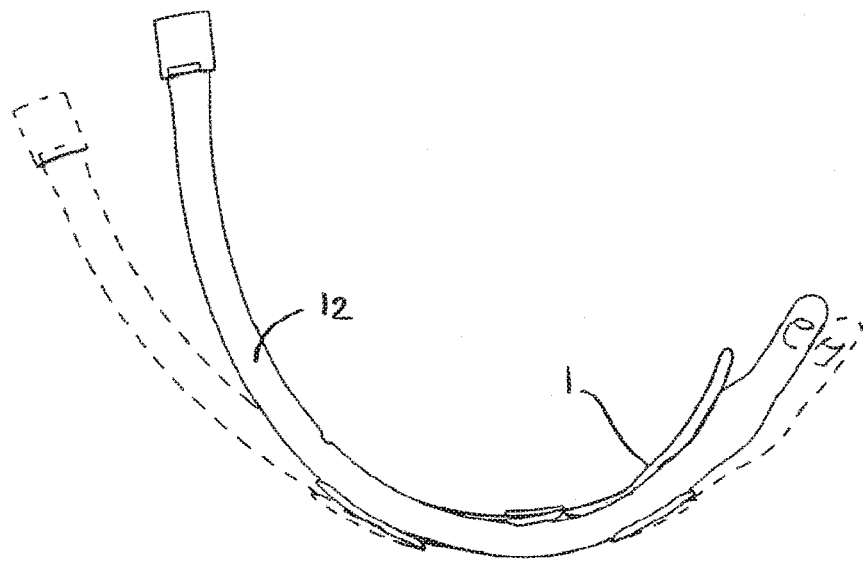
FIG. 2 is a side view of the laryngoscope insertion section of FIG. 1, with a retained endotracheal tube, with the movable tube guiding member in a tube raising configuration.

With reference to FIGS. 1 and 2, a laryngoscope insertion section, shown generally as 1, has a body 2, formed as a unitary moulding from a transparent plastics material. The body has a smooth inferior surface 4, which contacts a patient's palette in use, an opposing superior surface 6, a first smooth lateral surface 8 (at the rear in FIG. 1), and an opposing second lateral surface 10. The second lateral surface has a profile including a concave groove which runs along the majority of the length of the second lateral surface and which functions as part of a tube guide for an endotracheal tube 12. The insertion section has a distal end 14 comprising a spatulate member 16 which functions, in use, to lift a patient's anatomy adjacent the epiglottis.

The insertion section further defines an elongate cavity 18 which extends along a part of the length of the insertion section from an aperture (not shown) in the proximal end of the insertion section. The elongate cavity is closed off at its distal end by a window 20 (functioning as the viewing port). The elongate cavity curves gently and is sized to retain a support member 104 of a laryngoscope 100, illustrated in FIG. 10. The distal end of the elongate cavity is sealed to protect a camera 106 provided at the distal end of the laryngoscope support member from bodily fluids in use, while providing a viewing port through which the camera can image a patient's larynx during intubation. The insertion section is formed and arranged to fit over the support member like a sleeve. The insertion section is elongate and curved.

A pivoting member 50 is attached to the second lateral surface of the insertion section by way of a pivot 52. The pivoting member includes a distal superior tube guiding member 54 (functioning as the moveable tube guiding member), located distally of the pivot, having a concave elongate groove on an inferior surface thereof, the distal tip of which contacts the superior surface of a retained endotracheal tube in use. The pivoting member includes an inferior tube guiding member 56 (functioning as a further moveable tube guiding member), located proximally of the pivot, having a concave elongate groove on a superior surface thereof, at least the proximal tip of which contacts the inferior surface of a retained endotracheal tube in use. The pivoting member is rotatable around the pivot, in the plane of the insertion section, and its movement is limited by the periphery of an aperture 58 through the pivoting member, which engages with a pin 60 extending from the second lateral surface of the insertion section. As the pivoting member can be rotated in use, the position of the distal superior tube guiding member, which is transversely mounted on the body of the insertion section, can be moved relative to the body of the insertion section adjacent the distal superior tube guiding member.

A tube guide is formed by the distal superior tube guiding member and the inferior tube guiding members, as well as a proximal superior tube guiding member 62, which, in this embodiment, is fixedly mounted to the insertion section, located towards the proximal end of the insertion section, having a concave elongate groove on an inferior surface thereof, at least the distal tip of which contacts the superior surface of a retained endotracheal tube in use. The concave elongate groove of the proximal superior tube guiding member extends slightly in the superior direction towards its distal tip, to retain an endotracheal tube at a smaller radius of curvature than the radius of curvature of the insertion section at the distal to the third tube guiding member, as can be seen from FIG. 2. The proximal tip of the inferior tube guiding member is longitudinally spaced from the distal tip of the proximal superior tube guiding member so that the endotracheal tube can follow a path with a smaller radius of curvature than the insertion section. This arrangement enables the tube guide to be especially thin in the region of a patient's teeth and, as the inferior surface of a retained endotracheal tube is left exposed, the endotracheal tube may be grasped by the user. The insertion section is also useful with endotracheal tubes of a wide range of external diameters, which follow slightly different paths along the length of the insertion section.

Figures 3, 4:
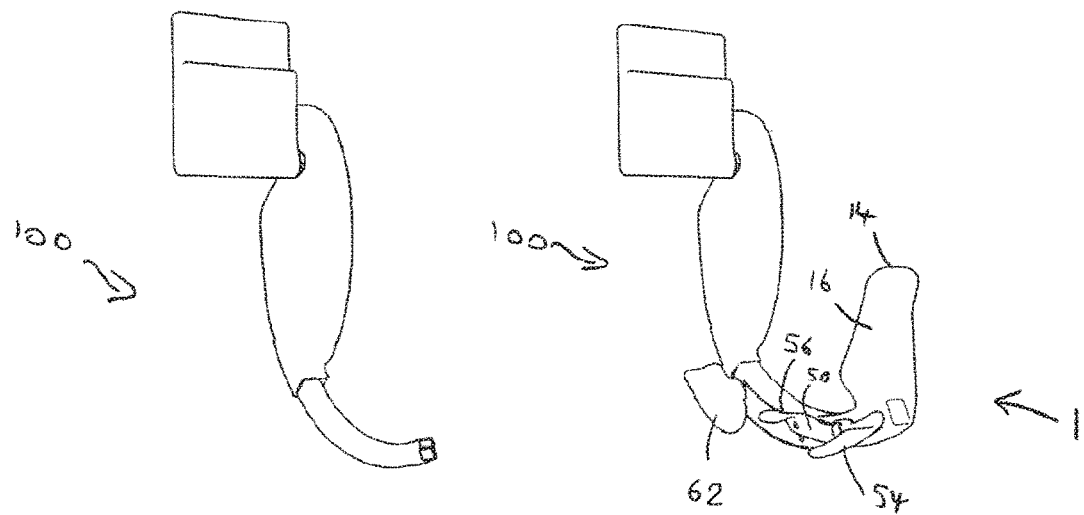
FIG. 3 is an isometric view of a laryngoscope for detachably retaining the insertion section of FIG. 1.
FIG. 4 is an isometric view of the laryngoscope of FIG. 3 whilst retaining the insertion section of FIG. 1.
Figure 5:
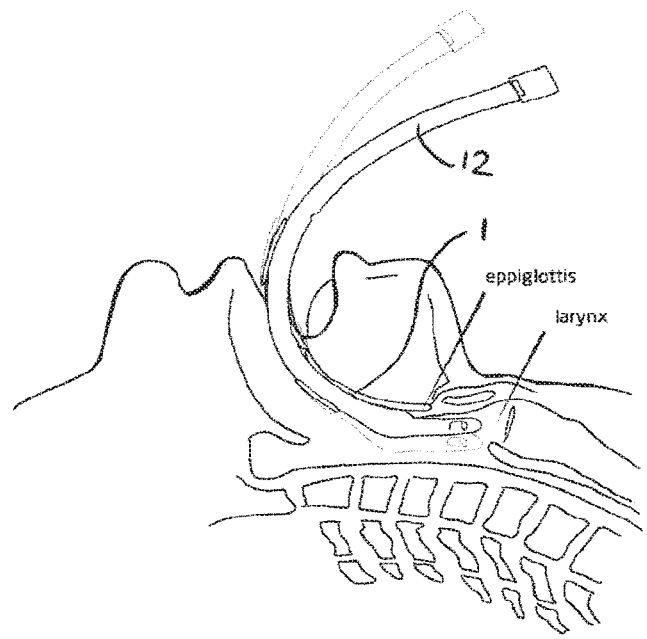
FIG. 5 is a cross-section through a patient, illustrating the position of the laryngoscope insertion section of FIG. 1 and a retained endotracheal tube, when the movable tube guiding member is in the tube raising configuration, or in the tube lowering configuration.
Figure 6:
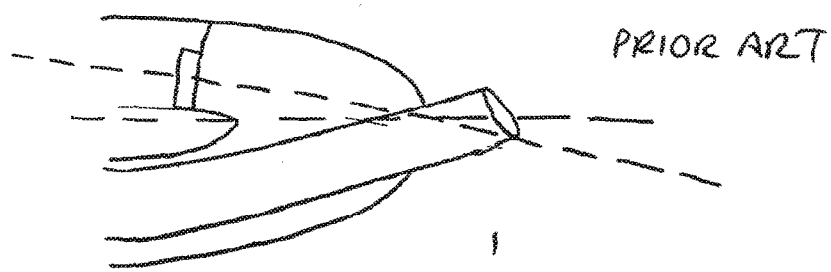
FIG. 6 (Prior Art) is a plan view of the distal tip of an insertion section having a known arrangement of viewing port and a tube guide.
Figure 7:
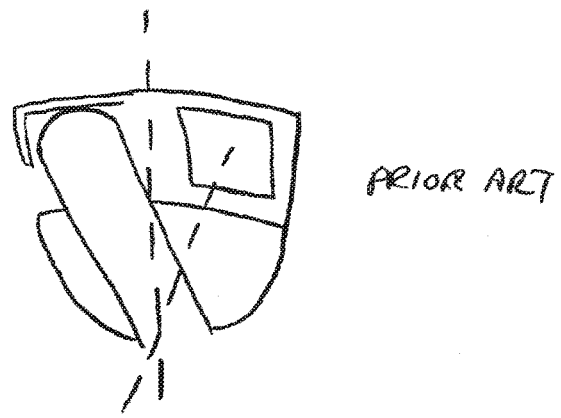
FIG. 7 (Prior Art) is a perspective view of the insertion section of FIG. 6 while retaining an endotracheal tube.

The insertion section is for use as a disposable accessory for a laryngoscope 100, illustrated in FIGS. 3 and 4. The laryngoscope includes a handle 102 from which support member 104 extends. The support member has, at a distal tip, camera 106 (functioning as a light collector) and an LED light source 108. The support member is formed from steel and provides mechanical support for an insertion section retained on the support member in use. A battery within the handle (not shown) provides power to the camera and light source. A video screen 110 receives and displays images from the camera in use. The support member may be integral to the body of the laryngoscope or demountable, for example, to enable the support member to be separately sterilised. The junction between the laryngoscope body and support member may be adjustable to vary the maximum distance to which the support member extends from the laryngoscope body. The support member curves gently within a plane. The plane of the support member is optionally laterally offset from the central axis of the laryngoscope.

Figure 8:
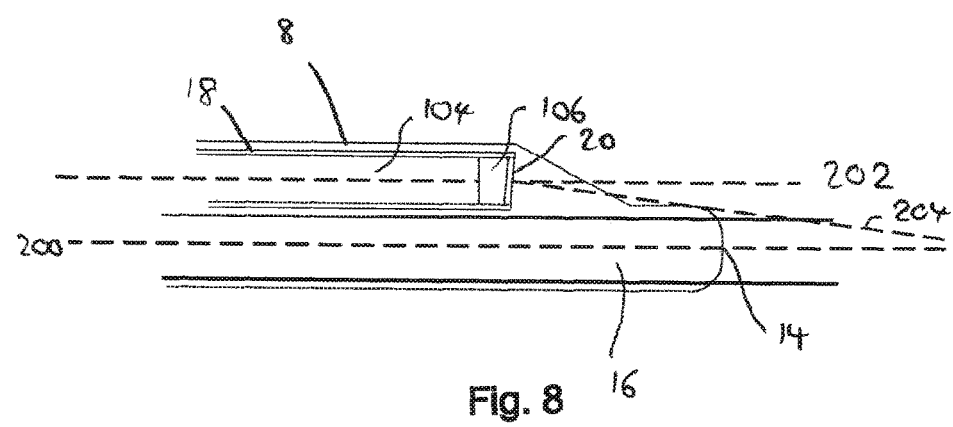
FIG. 8 is a plan view of the distal tip of an insertion section according to the present invention.
Figure 9:
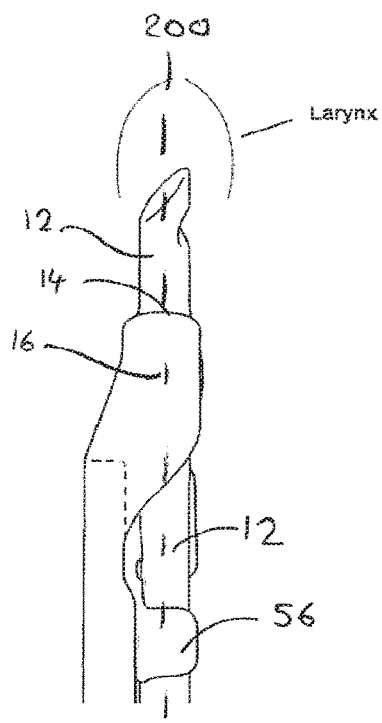
FIG. 9 is a plan view of the distal tip of an insertion section according to the present invention, retaining an endotracheal tube.
Figure 10:
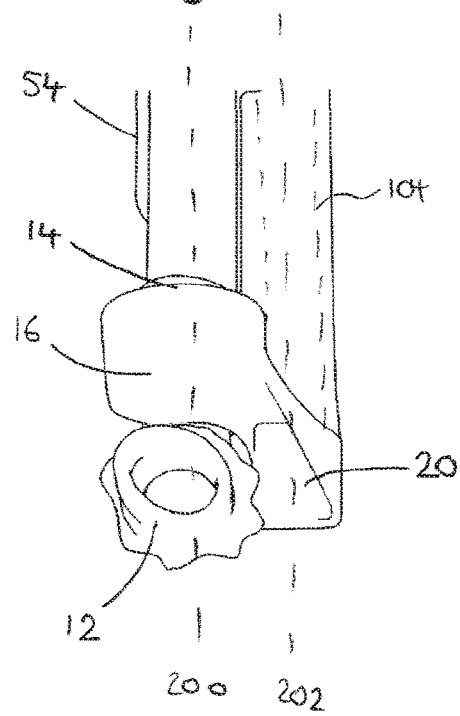
FIG. 10 is an isometric view, from distally of the insertion section, of an insertion section of the present invention, retaining an endotracheal tube.

With reference to FIGS. 8 through 10, the tube guiding members (functioning as some or all of the tube guide) guide a retained endotracheal tube within a plane 200. The tube is constantly curved from where the most proximal location where it contacts the insertion section (typically towards or at the distal end of the proximal superior tube guiding member) to the most distal location where it contacts the insertion section (typically towards or at the distal end of the distal superior tube guiding member). The support member of a laryngoscope supporting the insertion section is within a second plane 202, parallel to but spaced apart from the plane of the retained endotracheal tube. The distal surface of the viewing port is angled relative to the plane of the endotracheal tube and the plane of the support member, such that its normal 204 intersects with the plane of the retained endotracheal tube distally of the distal tip of the insertion section.

In use, a new disposable insertion section, which has typically been kept in a sterile package since manufacture, is slid onto the retaining member until the tip of the retaining member is adjacent the transparent window. The insertion section protects the retaining member and the camera and light source at the distal end of the retaining member. Furthermore, light from the light source is directed towards and beyond the distal tip of the insertion section and the camera is operable to collect images of the distal tip of the insertion section and the surrounding space, centered on approximately the location where a patient's larynx will be visible during intubation. As the retaining member is formed from steel, it functions as a strengthening element, reinforcing the insertion section.

Next, an endotracheal tube is inserted into the tube guide. The endotracheal tube is held in flexural tension by the proximal and distal superior tube guiding members and the inferior tube guiding member. The proximal and distal superior tube guiding members exert forces in an inferior direction on the endotracheal tube and the inferior tube guiding member exerts forces in a superior direction, such that the endotracheal tube is both held in placed and guided along a path. The flexural tension serves to retain the tube in position and avoids the requirement for further tube retaining members. Furthermore, the position of the proximal and distal superior tube guiding member and the inferior tube guiding member defines the path by which a retained endotracheal tube having a given external diameter extends along the insertion section (functioning as the proximal tube path) when no external force is applied to the endotracheal tube. The position of the proximal and distal superior tube guiding members and the inferior tube guiding member further defines the path (the distal tube path) by which a retained endotracheal tube having a given external diameter would extend beyond the insertion section, towards a patient's larynx in use, when no external force is applied to the endotracheal tube.

Initially, a retained endotracheal tube extends distally of the distal superior tube guiding member but is preferably not sufficiently far advanced as to not extend beyond the distal tip of the insertion section. The endotracheal tube is retained in flexural tension from the most proximal location where it contacts the tube guide to the most distal location where it contacts the tube guide. As a result of this flexural tension, and the gentle curvature which is typical of endotracheal tubes, the tube exerts a force in the superior direction on the distal superior tube guiding member, as well as a force in the inferior direction on the inferior tube guiding member. Thus, the pivoting member will typically rest in a position determined by the movement limiter.

The laryngoscope is then manipulated to introduce the insertion section into a patient's oral cavity, using the spatulate tip portion to lift the patient's anatomy around the epiglottis, exposing the larynx. During this stage, images from the camera are transmitted by a wired or wireless connection to a display screen which can conveniently be attached to the handle of the laryngoscope but may alternatively be separate to the laryngoscope. As the endotracheal tube is already retained within the tube guide, the user will not be required to carry out the additional step of introducing an endotracheal tube into a patient's oral cavity, freeing up one of their hands. However, the laryngoscope, insertion section and tube guide may also be configured so that an endotracheal tube can be introduced into the tube guide and advanced along the tube guide after insertion of the laryngoscope into a patient's oral cavity.

The user will adjust the position of the laryngoscope so as to provide a good view of the patient's larynx. As will be apparent from FIGS. 8 through 10, the distal tip of the insertion section, which is the most distal location where the insertion section contacts a patient, on the inferior surface of the insertion section, is generally within the plane of the retained endotracheal tube. Users typically manipulate laryngoscopes so as to lift the tissue adjacent the epiglottis substantially in the patient's median plane, and therefore substantially the middle of the larynx. Thus, when a user has introduced the insertion section into the best position to view the larynx, they will typically also have located the retained tube so that the retained tube is in a plane intersecting the middle of the larynx. Thus, little or no lateral movement of the insertion section will be required for the endotracheal tube to be in the correct position to be advanced distally into the patient's larynx. Typically, the plane of the retained endotracheal tube will be substantially co-planar with the patient's median plane.

Typically, the distal tip of the endotracheal tube will not initially be aligned perfectly to advance into the larynx. Due to the configuration of the tube guide and the distal tip of the spatulate member, when the distal tip of the insertion section is in the correct position to best lift the patient's anatomy around the epiglottis and expose the larynx, an endotracheal tube located in the tube guide will typically be located at, or close to, the correct lateral position to advance a tube into a patient's larynx. However, there may well be a significant difference between the position of the distal tip of the endotracheal tube parallel to the inferior-superior axis.

The user then adjusts the orientation of the distal tip of the endotracheal tube in the plane of the tube guide by contacting the endotracheal tube with their fingers adjacent to and possibly distally of the proximal superior tube guiding member which, when the larynx is fully in view, is typically adjacent to or just outside of a patient's teeth. As users of laryngoscopes typically grip laryngoscopes at the base of the handle and proximal end of the insertion section, this is a natural movement. By slight movements of their fingers, users can change the orientation at which the endotracheal tube contacts the distal end of the proximal superior tube guiding member. By increasing the angle of incidence of the endotracheal tube on the distal end of the proximal superior tube guiding member, the pivoting member pivots such that the inferior tube guiding member moves in an superior direction and the distal superior tube guiding member moves in an inferior direction. As a result, the tip of the retained endotracheal tube moves in an inferior direction. As the inferior tube guiding member and distal superior tube guiding member are linked and move together, and as the insertion section extends distally of the distal superior tube guiding member, a relatively small adjustment of the angle of incidence of the endotracheal tube on the distal end of the proximal superior tube guiding member can have a substantial effect on the movement of the distal tip of the endotracheal tube. Movement of the distal tip of the endotracheal tube in an inferior direction is effectively geared to movement of the distal superior tube guiding member in an inferior direction, with a gearing ratio of greater than 1.0 so that a compact insertion section can readily control significant movements in the distal tip of the retained endotracheal tube. The camera and display screen are typically configured so that the inferior direction is uppermost and so manually increasing the angle of incidence of the endotracheal tube will appear to move the tip of the endotracheal tube upwards on the display. The maximum extent to which the distal tip of the retained endotracheal tube can be moved in the inferior direction, referred to here as the tube raising position, is illustrated, for example, in FIG. 2.

Once the user is happy with the location of the distal tip of the endotracheal tube relative to the larynx, the user can advance the tube with their fingers, thereby intubating the patient. As the retained tube is located in a plane, the resistance to movement of the tube is less than would be the case if the tube guide cause the tube to curve laterally. Furthermore, the hand movement required to advance the endotracheal tube in a distal direction is similar to the hand movement required to intubate using a conventional laryngoscope, such as a traditional laryngoscope with a Macintosh insertion section. Still further, as the retained tube is advanced in the plane, the distal tip does not move laterally while it is advanced, making the movement of the tip more predictable to a user who is viewing intubation using the laryngoscope screen.

Advantageously the user has also been able to locate the spatulate tip of the laryngoscope insertion section while concentrating on lifting the tissue adjacent the epiglottis to best expose the larynx, without having to adjust the location of the insertion section to orient the retained endotracheal tube relative to the patient's larynx. They can subsequently focus their attention on the position of the distal tip of the endotracheal tube parallel to the inferior-superior axis, using their fingers, to direct the endotracheal tube towards a patient's larynx. As movement of the tip of the endotracheal tube in the inferior or superior direction can be accomplished without significantly advancing the endotracheal tube, the endotracheal tube can be advanced as a separate action.

Finally, the endotracheal tube is detached from the tube guide and the laryngoscope and attached insertion section are removed from the oral cavity, leaving the endotracheal tube. The insertion section can then be disposed of and the laryngoscope reused for further intubations.

Typically, the insertion section is designed to be used with an endotracheal tubes of a range of sizes. The range of external diameters of endotracheal tubes with which an insertion section can be reliably used is referred to as the an operating range of endotracheal tube sizes. The operating range of endotracheal tube size, and the dimensions of the insertion section will depend on the application of the insertion section. An insertion section for use with adult humans may, for example, be adapted to be usable reliably with endotracheal tubes with an external diameter of up to 12.3 mm. Tubes of this external diameter are referred to as Size 9.0 in the field. The minimum external diameter may be around 5.5 mm. Where the insertion section is made from a plastics material, the mean thickness of the inferior and first superior tube guiding members typically requires to be at least 0.75 mm (preferably around 1.5 mm) to provide suitable mechanical strength for internal use. Accordingly, the thickness of the first region is preferably less than 15.3 mm, more preferably less than 14.6 mm, 13.8 mm or more preferably less than 13.1 mm, in the case of an insertion section for inserting endotracheal tubes into adult humans.

The dimensions of an insertion section for use with infant humans, including new born infants, are typically scaled proportionately from the dimensions of an insertion section for use with human adults. Nevertheless, the proportions of some features, such as the thickness of the tube guiding members, may not scale proportionately. In the case of an insertion section for inserting endotracheal tubes into infant humans, including new born infants, the operating range of external tube diameters may be 1.0 to 5.0 mm, and the thickness of the first region is preferably less than 8.0 mm, preferably less than 7.0 mm, or more preferably less than 6.0 mm.

The invention can equally be employed using a tube guide with fixed, rather than moveable, tube guiding members.

Further variation and modifications may be considered by one skilled in the art, within the scope of the invention herein disclosed.

The invention claimed is:

1. A laryngoscope blade, comprising:
a blade body configured to be removably coupled to a rigid support member of a laryngoscope and having a proximal end and a distal end, the blade body having a housing having a cavity along a portion of the blade body between the proximal end and the distal end, wherein the cavity comprises an opening adjacent to the proximal end of the blade body and terminates in a closed transparent end face proximal to the distal end of the blade body, and wherein the cavity is configured to receive the rigid support member through the opening such that a camera disposed on a terminating end of the rigid support member is adjacent to the closed transparent end face;
a first tube guide disposed along a lateral surface of the blade body, wherein a proximal terminus of the first tube guide extends proximally past the opening of the cavity; and
a second tube guide separate from the first tube guide comprising an inferior surface and disposed distally of the first tube guide along the lateral surface of the blade body, wherein the first tube guide and the second tube guide are configured to hold an endotracheal tube under flexural tension such that the first tube guide and the second tube guide position the tube in a plane laterally offset from the closed transparent end face, and wherein the closed transparent end face comprises a surface angled relative to a longitudinal axis of the housing such that a centerline axis of the surface of the transparent end face intersects the plane forward of the distal end of the blade body.

2. The laryngoscope blade of claim 1, wherein the first tube guide is positioned adjacent to the proximal end of the blade body and the second tube guide is positioned adjacent to the closed transparent end face.

3. The laryngoscope blade of claim 1, wherein a terminating end of the second tube guide is positioned between the closed transparent end face and the distal end of the blade body such that a distal most tip of the second tube guide is proximal to the distal end of the blade body.

4. The laryngoscope blade of claim 3, wherein the second tube guide comprises a superior portion configured to contact and hold an exterior curve of the endotracheal tube and an inferior portion configured to contact and hold an interior curve of the endotracheal tube.

5. The laryngoscope blade of claim 1, wherein the second tube guide comprises a movable member.

6. The laryngoscope blade of claim 5, wherein the movable member comprises a proximal member positioned adjacent to an inferior outer surface of the blade body and a distal member spaced apart from the proximal member and positioned adjacent to a superior outer surface of the blade body that is opposite the inferior outer surface.

7. The laryngoscope blade of claim 6, wherein the blade body comprises a protrusion extending away from the lateral surface and configured to engage with an aperture of the proximal member to control movement of the movable member about an axis of the blade body that is perpendicular to a longitudinal axis of the blade body.

8. The laryngoscope blade of claim 1, wherein the blade body comprises a spatula extending between the closed transparent end face of the cavity and the distal end of the blade body, wherein the spatula is configured to lift a patient's tissue during intubation of the patient.

9. The laryngoscope blade of claim 1, wherein the tube is held in the plane such that a distal end of the tube is held under the flexural tension, and wherein proximal portions of the tube are not under the flexural tension.

10. The laryngoscope blade of claim 1, wherein the surface is a distal surface of the closed transparent end face.

11. The laryngoscope blade of claim 1, wherein the inferior surface is curved.

12. A laryngoscope blade, comprising:
- a blade body configured to be removably coupled to a rigid support member of a laryngoscope and having a proximal end and a distal end, the blade body having a housing having a cavity along a portion of the blade body between the proximal end and the distal end, wherein the cavity comprises an opening adjacent to the proximal end of the blade body and terminates in a closed transparent end face proximal to the distal end of the blade body, and wherein the cavity is configured to receive the rigid support member through the opening such that a camera disposed on a terminating end of the rigid support member is adjacent to the closed transparent end face;
- a first tube guide disposed along a lateral surface of the blade body, wherein the first tube guide is positioned along the lateral surface such that an entirety of the opening of the cavity is positioned between a proximal tube guide end and a distal tube guide end of the first tube guide; and
- a second tube guide separate from the first tube guide comprising an inferior surface and disposed distally of the first tube guide along the lateral surface of the blade body, wherein the first tube guide and the second tube guide are configured to hold an endotracheal tube in a plane laterally offset from the closed transparent end face.

* * * * *